(12) United States Patent
Rosen et al.

(10) Patent No.: US 6,946,456 B2
(45) Date of Patent: Sep. 20, 2005

(54) METHODS FOR TREATING CELL PROLIFERATIVE DISORDERS AND VIRAL INFECTIONS

(75) Inventors: Neal Rosen, Englewood, NJ (US); Mary Srethapakdi, Bangkok (TH)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 10/343,246

(22) PCT Filed: Jul. 27, 2001

(86) PCT No.: PCT/US01/23640

§ 371 (c)(1),
(2), (4) Date: May 23, 2003

(87) PCT Pub. No.: WO02/09696

PCT Pub. Date: Feb. 7, 2002

(65) Prior Publication Data

US 2003/0216369 A1 Nov. 20, 2003

Related U.S. Application Data

(60) Provisional application No. 60/245,264, filed on Nov. 2, 2000, and provisional application No. 60/221,415, filed on Jul. 28, 2000.

(51) Int. Cl.$^7$ ..................... A61K 31/336; A61K 31/395
(52) U.S. Cl. ....................................... 514/183; 514/450
(58) Field of Search ............................... 514/183, 450; 540/461; 549/354

(56) References Cited

U.S. PATENT DOCUMENTS

| | | | |
|---|---|---|---|
| 4,261,989 A | 4/1981 | Sasaki et al. ............... | 514/183 |
| 5,387,584 A | 2/1995 | Schnur ....................... | 514/183 |
| 5,650,430 A | 7/1997 | Sugimura et al. ........... | 514/450 |
| 5,932,566 A | 8/1999 | Schnur et al. .............. | 514/183 |
| 5,968,921 A | 10/1999 | Gold .......................... | 514/183 |
| 6,210,974 B1 | 4/2001 | Gold .......................... | 436/501 |
| 6,239,168 B1 | 5/2001 | Ino et al. .................... | 514/450 |
| 6,335,157 B1 | 1/2002 | Gonzalez et al. ............. | 435/4 |
| 6,413,975 B1 | 7/2002 | Chasin et al. ............... | 514/261 |
| 6,440,982 B1 | 8/2002 | Maw et al. ................. | 514/263.2 |

FOREIGN PATENT DOCUMENTS

WO    WO 00/61578    10/2000

OTHER PUBLICATIONS

Chiosis et al. A small molecule designed to bind . . . Chemistry & Biology. Mar. 7, 2001, vol. 8, No. 3, pp. 289–299.*
Hosokawa et al. Hydroxymycotrienins A and B, New Ansamycin Group Antibiotics. The Journal Of Antibiotics. May 1996, vol. 49, No. 5, pp. 425–431.*
Srethapakdi et al. Herbimycin A reveals a role for Rb in mitosis. Proceedings of the American Association for Cancer Research. Mar. 1999, vol. 40, p. 11, Abstract #72.*

Chavany, et al., "p185$^{tabB2}$ Binds to GRP94 in Vivo", Journal of Biological Chemistry, vol. 271, No. 9 Mar. 1, 1996, pps. 4974–4977.
Neckers, "Effects of Geldanamycin and Other Naturally Occuring Small Molecule Antagonists of Heat Shock Protein 90 on HER2 Protein Expression", Breast Disease 11 (2000) 49–59. pps. 49–59.
Schnur, et al. "erbB–2 Oncogene Inhibition by Geldanamycin Derivatives: Synthesis, Mechanism of Action, and Structure—Activity Relationships", J. Med. Chem. 1995, 38, 3813–3820.
Munster, et al. Inhibition of Heat Shock Protein 90 Function by Ansamycins Causes the Morphological and Functional Differentiation of Breast Cancer Cells, Cancer Research. Apr. 1, 2001, vol. 61, pp. 2945–2952, especially the Abstract, p. 2950, col. 2, first full paragraph, p. 2951, col. 1, third full paragraph.
Neckers, "Effects of Geldanamycin and Other Naturally Occuring Small Molecule Antagonists of Heat Shock Protein 90 on HER2 Protein Expression", Breast Disease 11 (2000) 49–59. pps. 49–59.
Schnur, et al. "erbB–2 Oncogene Inhibition by Geldanamycin Derivatives: Synthesis, Mechanism of Action, and Structure—Activity Relationships", J. Med. Chem. 1995, 38, 3813–3820.
Chavany, et al., "p185$^{subB2}$ Binds to GRP94 in Vivo", Journal of Biological Chemistry, vol. 271, No. 9 Mar. 1, 1996, pps. 4974–4977.
Schulte et al. "The benzoquinone ansarnycin 17–allylamino–17–demethoxyge Idanamycin binds to HSP90 and shares important biologic activities with geldanamycin", Canc er Chemotherapy and Pharmacology, 1998, vol. 42, pp 273–279.
Hurst, et al., "HSP90 inhibitors block the mitotic checkpoint and are synergistically toxic with spindle poisons", Clinical Cancer Res., Nov. 1999, vol. 8, p. 3788s, #293.
Kherfellah, d., et al., "Effect of the combination of topoisomerase I and topoisomerase II inhibitors on rat glioblastoma cells and drug–resistant varian ts", Pharmacol. Experimental Therapeutics, Mar. 1999, vol. 40, p. 109, #724, Proceedings of the American Association for Cancer Research.

(Continued)

* cited by examiner

Primary Examiner—Jeffrey Edwin Russel
(74) Attorney, Agent, or Firm—Oppedahl & Larson LLP

(57) ABSTRACT

The present invention concerns methods for treating cell proliferative diseases, tumors associated with viral infections, and certain viral infections. The disclosed methods use compounds which inhibit heat shock protein 90 proteins. Such methods block Rb negative or deficient cells in the G2/M phase of the cell cycle and rapidly causes their destruction.

19 Claims, 10 Drawing Sheets

OTHER PUBLICATIONS

Stebbins, C.E., et al., "Crystal structure of the HSP90–Geldanamycin complex: targeting of a protein chaperone by an antitumor agent", Cell, Apr. 1997, vol. 89, pp. 239–240 and 246–248.

Rosenhagen, M.C. et al. "Synergistic inhibition of the Glucocorticoid receptor by radicicol and benzoquinone ansamycins", Biol. Chem., Mar. 2001, vol. 382, pp. 499–504.

Kato, et al. "Synthesis of Compounds Related to Antitumor Agents IV on the Reaction of Aromatic Carboxylates with 2, 4 Diamino–5–hydroxy–6–methylpyrimidine", Chem. Pharm. Bull. 1976, vol. 24, No. 10, pp 2461–2469. See Table 2.

Black et al., "Reaction of Ninhydrin With Activated anilines: Formation of Indole Derivatives", letrahedron. 1994, vol. 50, No. 37, pp 10983–10994. See Compound 17.

METHODS FOR TREATING CELL PROLIFERATIVE DISORDERS AND VIRAL INFECTIONS

This application is a 371 national phase of PCT application Ser. No. PCT/US01/23640 filed Jul. 27, 2001, and claims the benefit of U.S. Provisional Applications Ser. No. 60/221,415 filed Jul. 28, 2000 and 60/245,264 filed Nov. 2, 2000.

BACKGROUND OF THE INVENTION

The eukaryotic heat shock protein 90s (HSP90s) are ubiquitous chaperone proteins, which bind and hydrolyze ATP. The HSP90 family of proteins includes four known members: Hsp90 α and β, Grp94 and Trap-1. The roles of HSP90s in cellular functions are not completely understood, but recent studies indicate that HSP90s are involved in folding, activation and assembly of a wide range of proteins, including key proteins involved in signal transduction, cell cycle control and transcriptional regulation. For example, researchers have reported that HSP90 chaperone proteins are associated with important signaling proteins, such as steroid hormone receptors and protein kinases, including many implicated in tumorigenesis, such as Raf-1, EGFR, v-Src family kinases, Cdk4, and ErbB-2 (Buchner J., 1999, *TIBS,* 24:136–141; Stepanova, L. et al., 1996, *Genes Dev.* 10:1491–502; Dai, K. et al., 1996, *J. Biol. Chem.* 271:22030–4).

In vivo and in vitro studies indicate that without the aid of co-chaperones HSP90 is unable to fold or activate proteins. For steroid receptor conformation and association in vitro, HSP90 requires Hsp70 and p60/Hop/Sti1 (Caplan, A., 1999, *Trends in Cell Biol.,* 9: 262–68). In vivo HSP90 may interact with HSP70 and its co-chaperones. Other co-chaperones associated with HSP90s in higher eukaryotes include Hip, Bag1, HSP40/Hdj2/Hsj1, Immunophillinis, p23, and p50 (Caplan, A. supra).

Ansamycin antibiotics are natural products derived from *Streptomyces hygroscopicus* that have profound effects on eukaryotic cells. Many ansamycins, such as herbimycin A (HA) and geldanamycin (GM), bind tightly to a pocket in the HSP90 (Stebbins, C. et al., 1997, *Cell,* 89:239–250). The binding of ansamycins to HSP90 has been reported to inhibit protein refolding and to cause the proteasome dependent degradation of a select group of cellular proteins (Sepp-Lorenzino, L., et al., 1995, *J. Biol. Chem.,* 270:16580–16587; Whitesell, L. et al., 1994, *Proc. Natl. Acad. Sci. USA,* 91: 8324–8328).

The ansamycins were originally isolated on the basis of their ability to revert v-src transformed fibroblasts (Uehara, Y. et al., 1985, *J. Cancer Res.,* 76: 672–675). Subsequently, they were said to have antiproliferative effects on cells transformed with a number of oncogenes, particularly those encoding tyrosine kinases (Uehara, Y., et al., 1988, *Virology,* 164: 294–98). Inhibition of cell growth is associated with apoptosis and, in certain cellular systems, with induction of differentiation (Vasilevskaya, A. et al., 1999, *Cancer Res.,* 59: 3935–40). A GM derivative is currently in phase I clinical trials.

The use of ansamycins as anticancer agents are described in U.S. Pat. Nos. 4,261,989, 5,387,584 and 5,932,566. The preparation of the ansamycin, geldanamiycin, is described in U.S. Pat. No. 3,595,955 (incorporated herein by reference).

The ansamycin-binding pocket in the N-terminus of Hsp90 is highly conserved and has weak homology to the ATP-binding site of DNA gyrase (Stebbins, C. et al., supra; Grenert, J. P. et al., 1997, *J. Biol. Chem.,* 272:23843–50). This pocket has been reported to bind ATP and ADP with low affinity and to have weak ATPase activity (Proromou, C. et al., 1997, *Cell,* 90: 65–75; Panaretou, B. et al., 1998, *EMBO J.,* 17: 4829–36). In vitro and in vivo studies are said to indicate that occupancy of the pocket by ansamycins alters HSP90 function and inhibits protein refolding. At high concentrations, ansamycins have been reported to prevent binding of protein substrates to HSP90 (Scheibel, T., H. et al., 1999, *Proc. Natl. Acad. Sci. USA* 96:1297–302; Schulte, T. W. et al., 1995, *J. Biol. Chem.* 270:24585–8; Whitesell, L., et al., 1994, *Proc. Natl. Acad. Sci. USA* 91:8324–8328). Alternatively, they have also been reported to inhibit the ATP-dependent release of chaperone-associated protein substrates (Schleider, C., L. et al., 1996, *Proc. Natl. Acad. Sci. USA,* 93:14536–41; Sepp-Lorenzino et al., 1995, *J. Biol. Chem.* 270:16580–16587). In both models, the unfolded substrates are said to be degraded by a ubiquitin-dependent process in the proteasome (Schneider, C., L., supra; Sepp-Lorenzino, supra.)

In both tumor and nontransformed cells, binding of ansamycins to HSP90 has been reported to result in the degradation of a subset of signaling regulators. These include Raf (Schulte, T. W. et al., 1997, *Biochem. Biophys. Res. Commun.* 239:655–9; Schulte, T. W., et al., 1995, *J. Biol. Chem.* 270:24585–8), nuclear steroid receptors (Segnitz, B., and U. Gehring. 1997, *J. Biol. Chem.* 272:18694–18701; Smith, D. F. et al., 1995, *Mol. Cell. Biol.* 15:6804–12), v-src (Whitesell, L., et al., 1994, *Proc. Natl. Acad. Sci. USA* 91:8324–8328) and certain transmembrane tyrosine kinases (Sepp-Lorenzino, L. et al., 1995, *J. Biol. Chem.* 270:16580–16587) such as EGF receptor (EGFR) and Her2/Neu (Hartmann, F., et al., 1997, *Int. J. Cancer* 70:221–9; Miller, P. et al., 1994, *Cancer Res.* 54:2724–2730; Mimnaugh, E. G., et al., 1996, *J. Biol. Chem.* 271:22796–801; Schnur, R. et al., 1995, *J. Med. Chem.* 38:3806–3812). The ansamycin-induced loss of these proteins is said to lead to the selective disruption of certain regulatory pathways and results in growth arrest at specific phases of the cell cycle (Muise-Heimericks, R. C. et al., 1998, *J. Biol. Chem.* 273:29864–72).

Cyclin D in complex with Cdk4 or Cdk6 and cyclin E-Cdk2 phosphorylate the protein product of the retinoblatoma gene, Rb. Researchers have reported that the protein product of the Rb gene is a nuclear phosphoprotein, which arrests cells during the $G_1$ phase of the cell cycle by repressing transcription of genes involved in the $G_1$ to S phase transition (Weinberg, R. A., 1995, *Cell,* 81:323–330). Dephosphorylated Rb is said to inhibit progression through late $G_1$, in part, through its interaction with E2F transcription family members, which ultimately represses the transcription of E2F target genes (Dyson, N., 1998, *Genes Dev.,* 12: 2245–2262). Progressive phosphorylation of Rb by the cyclin-dependent kinases in mid to late $G_1$ leads to dissociation of Rb from Rb-E2F complexes, allowing the expression of E2F target genes and entry into the S phase.

The retinoblastoma gene product is mutated in several tumor types, such as retinoblastoma, osteosarcoma and small-cell lung cancer. Research also indicates that in many additional human cancers the function of Rb is is disrupted through neutralization by a binding protein, (e.g., the human papilloma virus-E7 protein in cervical carcinoma; Ishiji, T, 2000, *J Dermatol.,* 27: 73–86) or deregulation of pathways ultimately responsible for its phoshorylation. Inactivation of the Rb pathway often results from pertubation of p16INK04a, Cyclin D1, and Cdk4.

The retinoblastoma gene product, besides being a target of human papilloma E7 protein, is also the target of other oncogenic viral gene products. For example, studies indicate that the simian virus 40 large T antigen inactivates the Rb family of proteins, including Rb, p107, and p130 (Zalvide, J. H. et al., 1998, *Mol. Cell. Biol.,* 18: 1408–1415). Research also indicates that transformation by adenovirus requires E1A binding to Rb (Egan, C. et al., 1989, *Oncogene,* 4:383–388).

Scientists estimate that over 70 types of papilloma viruses infect humans (HPV) (Sasagawa, T. et al., 1996, *Clinical Diag. Lab. Immunol,* 3: 403–410). Of these several are associated with malignancies of humans, particularly cervical cancers (Bosch et al., 1995, *J. Natl. Cancer Inst.,* 87:796–802). Recent evidence also implicates HPV in some head and neck cancers. Several types of HPV are associated with an intermediate to high risk of malignancies (types 16, 18, 31, 33, 35, 45, and 56) (Sasagawa, T., et al., supra). In infections with these HPV, the viral genome integrates into the genome of the infected cell with subsequent expression of transforming genes E6 and E7. Data indicate that the products of these genes may promote malignant transformation by altering the functions of two cellular tumor suppressor proteins (p53 and Rb). E6 causes the proteolytic degradation of p53 (Scheffiner, M. et al., 1990, *Cell,* 63: 1129–1136. E7 complexes with Rb causing its release from transcription factor E2F, leading to the activation of genes involved in cell proliferation (Dyson, N. et al., 1988, *Science,* 243: 934–937.).

Most cancer therapies are not successful with all types of cancers. For example, solid tumor types ultimately fail to respond to either radiation or chemotherapy. There remains a need for cancer treatments which target specific cancer types. The present invention satisfies these needs and provides related advantages as well. The present invention provides novel methods for treating cell proliferative disorders and viral infections associated with retinoblastoma negative or deficient cells.

SUMMARY OF THE INVENTION

The present invention relates to methods useful for the treatment of an animal, preferably a mammal, that has a cell proliferative disorder or viral infection associated with Rb negative or deficient cells. One such method comprises administering an effective amount of a pharmaceutical composition that comprises a pharmaceutically acceptable carrier and a compound that binds to the N-terminal pocket of heat shock protein 90 to cells that are Rb negative or Rb deficient. In a preferred embodiment the HSP90 binding compound is an ansamycin. In a particularly preferred embodiment, the ansamycin is 17-allylamino-(17)-demethoxygeldanamycin (17-AAG).

The present invention further provides methods of destroying cells that are deficient in the retinoblastoma gene product. In one such embodiment, the method comprises administering an effective amount of a compound that binds to the N-terminal pocket of HSP90 to cells that are Rb negative or Rb deficient. In one embodiment, the HSP90 binding compound is an ansamycin. In a particularly preferred embodiment, the ansamycin is 17-AAG.

In another embodiment, the invention provides a method of destroying Rb negative or Rb deficient cells, comprising administering an effective amount of a compound that binds to the N-terminal pocket of HSP90 selected from the group consisting of herbimycin, geldanamycin, and 17-AAG, radicicol or synthetic compounds that bind into the N-terminal pocket of HSP90 which is the ATP-binding site of HSP90.

The method can further comprise treating a mammal in combination with other therapies. Other such therapies include, but are not limited to, chemotherapy, surgery, and/or radiotherapy.

By means of the invention, a method of destroying cells which are Rb negative or Rb deficient is provided. The invention provides a means to treat cell proliferative disorders, tumors associated with viral infections and certain viral infections associated with an Rb negative phenotype. These and other advantages of the present invention will be appreciated from the detailed description and examples set forth below. The detailed description and examples enhance the understanding of the invention, but are not intended to limit the scope of the invention.

BRIEF DESCRIPTION OF THE FIGURES

FIG. 2 shows levels of mitotic cyclin expression and associated kinase activities in Herbimycin arrested MB-MD 468 cells.

FIG. 5 shows the effect of HA on Rb-negative cells transfected with the Rb gene.

DETAILED DESCRIPTION OF THE INVENTION

Figure 1A:
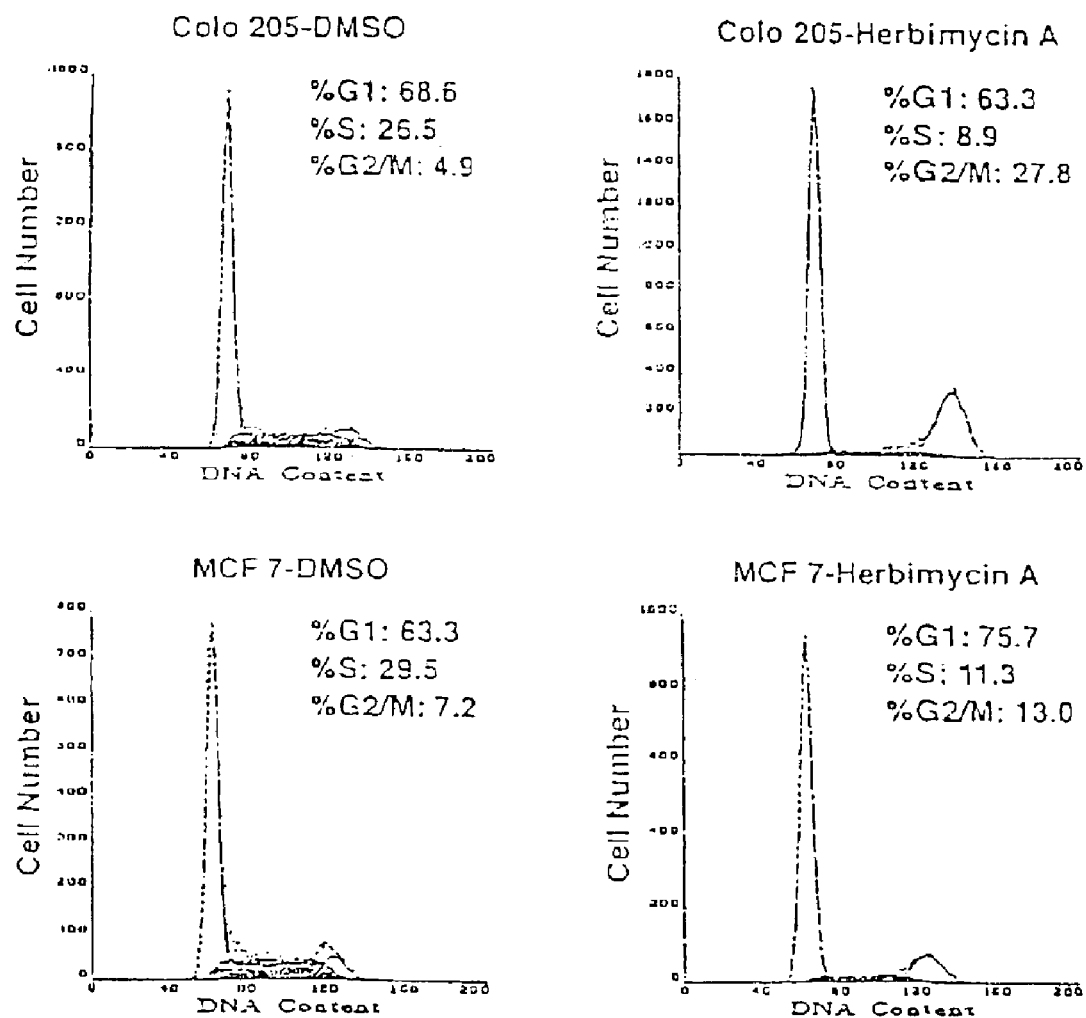
FIG. 1 shows differential cell cycle effects of Herbimycin on Rb-wild type (A) and Rb-negative cells (B). (A) MCF7 and Colo 205; (B) MB-MDA 468 and BT 549

The present invention concerns the surprising discovery that ansamycins cause Rb negative or Rb deficient cells to undergo mitotic arrest followed by rapid programmed cell death. This is in contrast to ansamycin treatment of cells containing wild-type levels of Rb, which causes cells to arrest in $G_1$ of the cell cycle followed, in some cases, by differentiation and apoptosis. The induction of mitotic arrest by ansamycins in Rb negative or Rb deficient cells, which rapidly leads to programmed cell death, is a phenomenon confined to cells with defective Rb function. Mitosis is unaffected in normal cells with wild-type Rb. Thus, the present invention will aid in the treatment of cell proliferative disorders which are associated with Rb negative or Rb deficient cells, such as small-cell lung cancers, retinoblastoma, osteosarcoma, certain breast cancers, prostate cancer, bladder cancer, hepatocarcinoma, certain viral infections, and virally induced tumors, including those caused by human papilloma viruses, such as cervical carcinoma.

As used in the specification and claims of this application, the term "Rb deficient" describes several types of cells, including cells which produce no detectable amounts of a functional Rb protein. Such cells are referred to herein as "Rb negative" cells. Cells which are Rb deficient may be cells which do not contain a functional Rb gene. Cells which are Rb deficient may also be cells that can encode an Rb protein, but in which the protein does not function properly or is produced at lower than normal level. An Rb deficient phenotype can also occur due to the perturbation of the pathway which ultimately results in phosphorylation of the Rb protein, for example, perturbation of p16INK4a, Cyclin D1, or Cdk4, and cells with such a perturbation are Rb deficient cells.

As used in the specification and claims of this application, the term "HSP90" refers to the family of HSP90 heat shock proteins. Thus, this term encompasses Hsp90 α and Hsp90β, Grp94 and Trap-1. The HSP90 heat shock proteins each possess a characteristic pocket located near the N-terminal end of the protein to which ATP and ADP bind. This is the same pocket which has been shown to bind to ansamycin antibiotics. This pocket is referred to herein as "the N-terminal pocket of HSP90".

Although the precise mechanisms are not yet understood, the present application makes use of compositions that bind to the N-terminal pocket of HSP90 in a manner that results in an alteration of the function of HSP90. As used in the specification and claims of this application, this alteration of function is referred to as "inhibition of HSP90 function". In accordance with the present invention, this inhibition occurs upon administration of HSP90 binding compounds, such as ansamycins, and results in arrest of Rb negative or deficient cells in mitosis. Such cells uniformly die through apoptotic mechanisms. This novel mechanism of destroying cells that are Rb negative or deficient provides a means to specifically treat cell proliferative disorders and certain viral infections associated with cells that are Rb negative or deficient.

The destruction of Rb negative or deficient cells can occur with less cytotoxicity to normal cells or tissues. For example, when cells which contain a normal Rb gene product are treated with HSP90 inhibitors, those cells arrest in $G_1$ of the cell cycle and, in some cases, may differentiate and die. However, cells which are Rb negative or deficient uniformly die when treated with HSP90 inhibitors. Further, such cells will be more susceptible to other agents or radiation treatments and will require lower doses of drug for killing than cells with wild-type retinoblastoma gene product. Studies indicate that the $G_2/M$ phase of the cell cycle is the most radiosensitive phase of the cell cycle (Sinclair, W. K, 1968, *Radiat. Res.*, 33:620).

In one embodiment of the invention, the $IC_{50}$ of the HSP90 inhibitor used in the instant methods to destroy cells which are Rb negative of Rb deficient is lower than the $IC_{50}$ against similar cells which are not Rb negative or deficient. Preferably the $IC_{50}$ is 5-fold lower, more preferably 10-fold lower, still further 20-fold lower, and most preferably 30- to 50-fold lower when compared to similar cells containing wild-type Rb.

As used herein "$IC_{50}$" is defined as the concentration of an HSP90 inhibitor required to achieve killing of 50% of cells.

The term "effective amount" as used herein, means an amount of a compound utilized in the methods of the present invention which is capable of providing a therapeutic effect. The specific dose of compound administered according to this invention to obtain therapeutic and/or prophylactic effects will, of course, be determined by the particular circumstances surrounding the case, including, for example, the compound administered, the route of administration, the condition being treated and the individual being treated. A typical daily dose (administered in single or divided doses) will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The preferred therapeutic effect of the methods of the instant invention, with respect to cell proliferative disorders is the inhibition, to some extent, of growth of cells causing or contributing to a cell proliferative disorder. A therapeutic effect relieves to some extent one or more of the symptoms of a cell proliferative disorder. In reference to the treatment of a cancer, a therapeutic effect refers to one or more of the following: 1) reduction in the number of cancer cells; 2) reduction in tumor size; 3) inhibition (i.e., slowing to some extent, preferably stopping) of cancer cell infiltration into peripheral organs; 3) inhibition (i.e., slowing to some extent, preferably stopping) of tumor metastasis; 4) inhibition, to some extent, of tumor growth; and/or 5) relieving to some extent one or more of the symptoms associated with the disorder.

In reference to the treatment of a cell proliferative disorder other than a cancer, a therapeutic effect refers to either: 1) the inhibition, to some extent, of the growth of cells causing the disorder; 2) the inhibition, to some extent, of the production of factors (e.g., growth factors) causing the disorder; and/or 3) relieving to some extent one or more of the symptoms associated with the disorder.

With respect to viral infections, the preferred therapeutic effect is the inhibition of a viral infection. More preferably, the therapeutic effect is the destruction of cells which contain the virus.

The methods of this invention are useful for inhibiting cell proliferative diseases associated with Rb negative or Rb deficient, for example, retinoblastoma, osteosarcoma, breast cancers, bladder cancer, prostate cancer, renal carcinoma, cancers associated with viral infections, such as cervical cancers associated with human papilloma virus, and small-cell lung cancer. Additionally, the methods of the invention are useful for the treatment of certain viral infections which result in an Rb negative phenotype, such as human papilloma virus.

"Cell proliferative disorders" refer to disorders wherein unwanted cell proliferation of one or more subset(s) of cells in a multicellular organism occurs, resulting in harm, for example, pain or decreased life expectancy to the organism. Cell proliferative disorders include, but are not limited to, tumors, benign tumors, blood vessel proliferative disorders, autoimmune disorders and fibrotic disorders.

The methods of the present invention may be used on mammals, preferably humans, either alone or in combination with other therapies or methods useful for treating a particular cell proliferative disorder or viral infection.

The use of the present invention is facilitated by first identifying whether the cell proliferation disorder or viral infection is accompanied by cells which contain altered expression of the Rb gene product. Once such disorders are identified, patients suffering from such a disorder can be identified by analysis of their symptoms by procedures well known to medical doctors. Such patients can then be treated as described herein.

The determination of whether the cell proliferation disorder is associated with an altered expression of the Rb gene product call be carried out by first determining the protein expression of Rb in the appropriate cells isolated from a mammal suspected of having a cell proliferative disorder or viral infection. For example, in the case of small-cell lung cancer, the protein expression of Rb determined from cells isolated from a mammal suspected of having small cell lung cancer can be compared to the appropriate cells isolated from a disease free mammal. Rb expression and/or mutations can be measured using methods well known in the art, including, but not limited to, immunohistochemistry, Southern blot analysis, and Northern blot analysis. The use of immunohistochemistry (e.g., Western blot analysis) to determine Rb expression is described by Higashiyam M et al., 1994, *Oncogene*, 51: 544–51, and Kohn G. J et al., 1997, *J. Gasroeterol. Hepatol.*, 12: 198–203, both of these references are incorporated herein by reference in their entireties. The use of Southern blot analysis to determine defects in the Rb gene is demonstrated by Presti J. C. Jr. et al., 1996, *Anticancer Res.*, 16:549–56, which is incorporated herein by reference in its entirety. The determination of Rb mRNA using Northern blot analysis is demonstrated by Rygaard K. et al., 1990, *Cancer Res.*, 50: 5312–7, which is incorporated by reference herein in its entirety. If the analysis indicates that there is altered Rb expression, the patient is a candidate for treatment using the methods described herein.

In the case of cell proliferative disorders arising due to unwanted proliferation of non-cancer cells, the level of the Rb gene product is compared to that level occurring in the general population (e.g., the average level occurring in the general population of people or animals excluding those people or animals suffering from a cell proliferative disorder). If the unwanted cell proliferation disorder is characterized by an abnormal level of Rb than occurring in the general population, then the disorder is a candidate for treatment using the methods described herein.

Methods to determine HPV association of with cervical cancer are described in Sasagawa, T. et al., supra, which is incorporated herein by reference.

Cell proliferative disorders, including those referenced above are not necessarily independent. For example, fibrotic disorders may be related to, or overlap with, blood vessel disorders. Additionally, for example, atherosclerosis (which is characterized herein as a blood vessel disorder) is associated with the abnormal formation of fibrous tissue.

A cancer cell refers to various types of malignant neoplasms, most of which can invade surrounding tissues, and may metastasize to different sites, as defined by Stedman's Medical Dictionary 25th edition (Hensyl ed. 1990).

The formation and spreading of blood vessels, or vasculogenesis and angiogenesis respectively, play important roles in a variety of physiological processes such as embryonic development, wound healing and organ regeneration. They also play a role in cancer development. Blood vessel proliferation disorders refer to angiogenic and vasculogenic disorders generally resulting in abnormal proliferation of blood vessels. Examples of such disorders include restenosis, retinopathies, and atherosclerosis.

As noted above, other such proliferative diseases can be identified by standard techniques, and by determination of the efficacy of action of the compounds described herein.

A. Rb Negative or Deficient Cells Arrest in Mitosis After Treatment With Ansamycins Rb negative or deficient cells treated with ansamycin or radicicol were discovered to contain a bipolar spindle and elevated cyclin B1-associated kinase activity. However, chromosomal alignment was disorganized, with chromosomes scattered along the length of the spindle. The presence of paired chromosomes at the poles led to the conclusion that HA-treated cells had arrested in prometaphase as a result of failure of chromosomes to align into a metaphase plate. This arrest was dependent on the absence of Rb as introduction of wild-type RB allowed progression through mitosis in the presence of drug. When treated with ansamycins in S phase, Rb-negative cells blocked in the subsequent mitosis whereas Rb-wild type cells progressed through mitosis and arrested in G. Thus, Rb is required for completion of mitosis when Hsp90 function is inhibited.

Figure 1B:
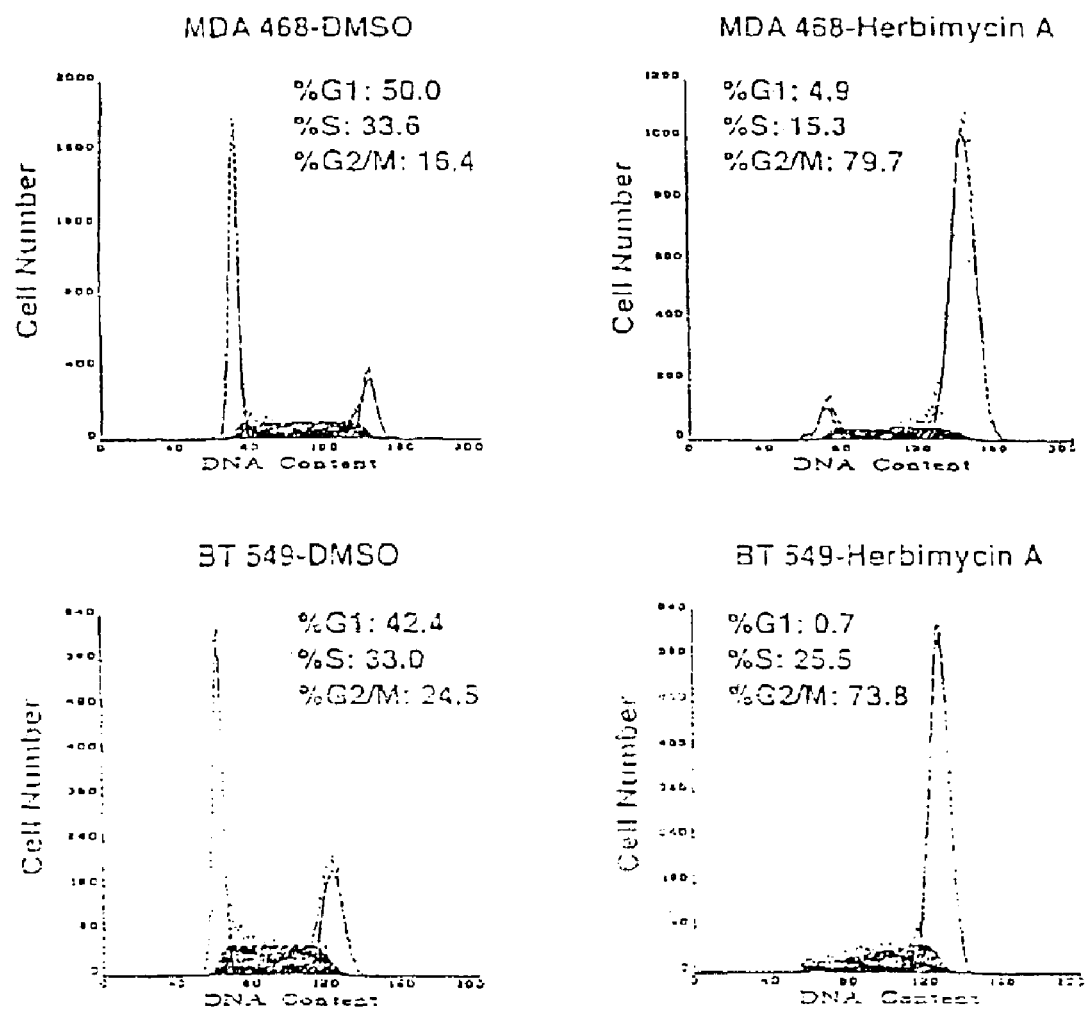

In 12 tumor cell lines examined, ansamycin treatment caused growth arrest in $G_1$ (FIG. 1A). This arrest was accompanied by a rapid decline in D-cyclin-associated kinase activity and hypophosphorylation of Rb, suggesting that ansamycins affect $G_1$ via a cyclin D-related pathway (Srethapakdi, M., F. Liu, R. Tavorath, and N. Rosen, 2000, *Cancer Res.* 60: 3940–6). These effects were elicited by three different ansarnycins, HA, GM and its derivative, 17-allylamino-(17)demethoxygeldanamycin (17-AAG), differing only in regard to potency. Although these experiments were done, for the most part, with HA, it will be understood that similar effects can be obtained using other ansamycins, which bind to the HSP90 pocket, such as the benzoquinone ansamycins, including, but not limited to, geldanamycin, geldanamycin derivatives, such as 17-AAG, herbimycin, and macbecins, or other compounds which bind to the HSP 90 pocket, such as radicicol. To determine if ansamycins disrupted $G_1$, progression by inhibiting the cyclin D-Rb pathway, their effects were examined in cell lines lacking functional Rb. Rb is the only known substrate of cyclin D-associated kinases (Baldin, V., et al., 1993, *Genes Dev.* 7:812–21; Ewen, M. E. et al., 1993, *Cell* 73:487–97; Kato, J., H. et al., 1993, *Genes Dev.* 7:331–42; Matsushime, H., et al., 1992, *Cell* 71:323–34; Matsushime, H., D. et al., 1994, *Mol. Cell. Biol.* 14:2066–76; Meyerson, M., and E. Harlow, 1994, *Mol. Cell. Biol.* 14:2077–86; Quelle, D. E., et al., 1993, *Genes Dev.* 7:1559–1571; Guan, K. -L., et al., 1994, *Genes Dev.* 8:2939–52; Koh, J. et al., 1995, *Nature* 375:506–10; Lukas, J. et al., 1995, *Mol. Cell. Biol.* 15:2600–1 1; Lukas, J., H. et al., 1994, *J. Cell Biol.* 125:625–38; Lukas. J., D. et al., 1995, *Nature* 375:503–6; Medema, R. H. et al., 1995, *Proc. Natl. Acad. Sci. USA*, 92:6289–93). In tumor cell lines with mutated Rb (MB-MDA 468, BT-549, DU145 and DU4475) HA treatment failed to induce a $G_1$ block but instead led to an accumulation of cells with 4n DNA content (FIG. 1B).

To determine if HA treatment caused Rb-negative cells to arrest in $G_2$ or mitosis, mitotic index was determined with bisbenzimide staining and mitosis was scored by the presence of condensed chromosomes. In MB-MDA 468 cells, in which the mitotic index of the control population was 5–10%, 60–70% of HA-treated cells were in mitosis. Thus, in the absence of Rb function, HA treatment resulted in mitotic arrest.

To further define the nature of the HA-induced mitotic defect, cells were triple-stained with bisbenzimide, anti-α-tubulin antibodies and anti-centromere autoimmune serum (ACA/CREST). α-tubulin staining revealed that arrested cells contained bipolar spindles, demonstrating that HA does not interfere with spindle formation. Examination of cluomosomnal distribution by bisbenzamide and ACA/CREST staining, however, showed that in most cells, chromosomes localized both to the poles and within the spindle.

Figure 3A:
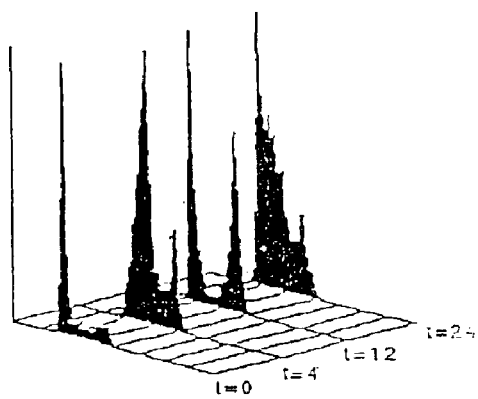
FIG. 3 shows Rb-wild-type cells complete mitosis in the presence of HA after arrest with aphidicolin (FIG. 3A).
FIG. 3B shows that, after release from aphidicolin, Rb-negative MB-MDA 468 cells arrested in the next mitosis FIG. 4A and B shows that HA induces mitotic arrest and not $G_1$ arrest in primary cells expressing HPV 16 E6 and E7.
Figure 3A:
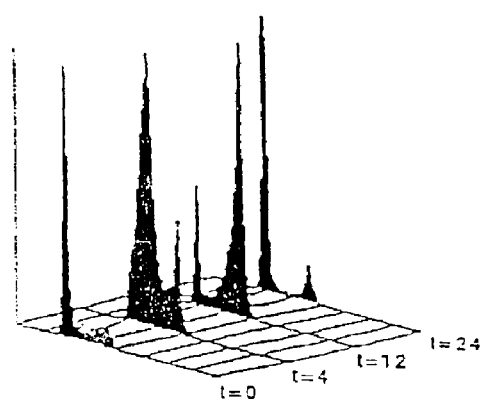
Figure 3B:
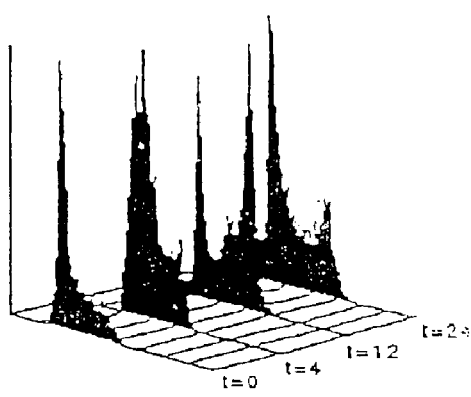
Figure 3B:
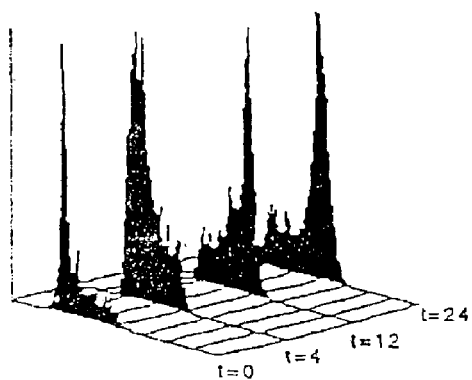

Without being bound to any particular theories, the observed accumulation of chromosomes at the poles is consistent with either an arrest in prometaphase due to failure of chromosomes to align into a metaphase plate or to an abnormal anaphase with impaired sister chromatid segregation. ACA staining, however, revealed paired centromeres on chromosomes at the poles, indicating that they were undisjoined sister chromatids (FIG. 3B). In 77 chromosomes localized to the poles, 87% scored as double dots for ACA staining. This demonstrates that accumulation of chromosomes at the poles did not result from premature or incomplete segregation but rather, failure of paired chromatids to congress to the spindle equator. These data show that HA-treated cells are arrested in prometaphase and that, in Rb-negative cells, HA induces mitotic arrest by interfering with chromosomal alignment.

Figure 2A:
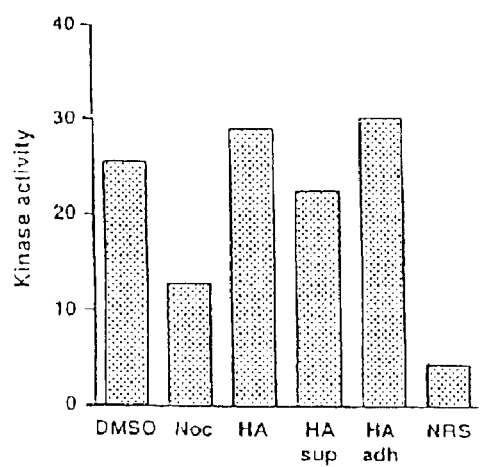
FIG. 2(A) shows a western blot using anti-cyclin A and also shows an in vitro kinase assay of immunoprecipitates isolated with anti-cyclin A.
Figure 2B:
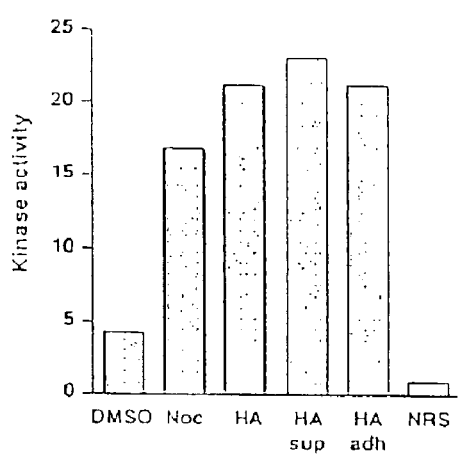
FIG. 2(B) shows a western blot using anti-cyclin B1 antibodies and also shows an iii vitro kinase assay of immunoprecipitates isolated with anti-cyclin B1.

To further distinguish between prometaphase and anaphase, the expression and -associated kinase activities of the mitotic cyclins were assessed. Levels of cyclin A-associated kinase activity begun to decline in prometaphase while cyclin B associated kinase activity remains elevated until anaphase (Furuno, N., N. den Eizen, and J. Pines, 1999, *J. Cell Biol.* 147:295–306; Townsley, F. M., and J. V. Ruderman, 1998, *Trends Cell Biol.* 8:238–244; Zachariae, W., and K. Nasmyth, 1999, *Genes Dev.* 13:2039–58). As the mitotic index in the HA-blocked population is only 60–70%, mitotically arrested cells were enriched by using only the loosely adherent population in which the mitotic index was greater than 90%. Cyclin B1-associated kinase activity was elevated 5-fold in HA-treated cells when compared to control and was comparable to that seen in nocodazole-arrested cells (FIG. 2B). In parallel with kinase activity, cyclin B1 protein expression was also increased in HA-treated cells (FIG. 2B). In contrast, cyclin A expression and its associated kinase activity were slightly lower in both HA and nocodazole-arrested cells compared to that in control cells (FIG. 2A). Thus, HA induces arrest at a point before early anaphase and after prophase when proteolysis of cyclin A but not cyclin B1, has begun. This result shows that arrest occurs in prometaphase of mitosis.

Cells with Wild-type RB Traverse Mitosis in the Presence of HA

The HA-induced mitotic block was observed, surprisingly, only in cells lacking wild-type Rb. HA likely causes the degradation of mitotic regulators more slowly than it affects the expression of $G_1$ regulators. The absence of Rb would abrogate the effects on $G_1$ and expose the mitotic phenotype. The addition of HA to Rb-negative cells blocked in S phase, then, would fail to cause arrest in the mitosis immediately following drug addition. To demonstrate this, Colo 205 cells and MB-MDA, 468 cells were arrested in $G_1$/S with aphidicolin and subsequently released from block in the presence of either HA or DMSO. In the presence of HA, Rb-wild type Colo 205 cells progressed through G2 and mitosis and were arrested in the next $G_1$ (FIG. 3A). In contrast, following release from aphidicolin, Rb-negative MB-MDA 468 cells arrested within 12 hours in the next mitosis (FIG. 3B). Thus, cells containing Rb are able to progress normally through mitosis in the presence of HA while those lacking Rb function are not.

HA Induces M and Not G, Arrest in Primary Cells Expressing HPV 16 E6 and E7

Figure 4A:
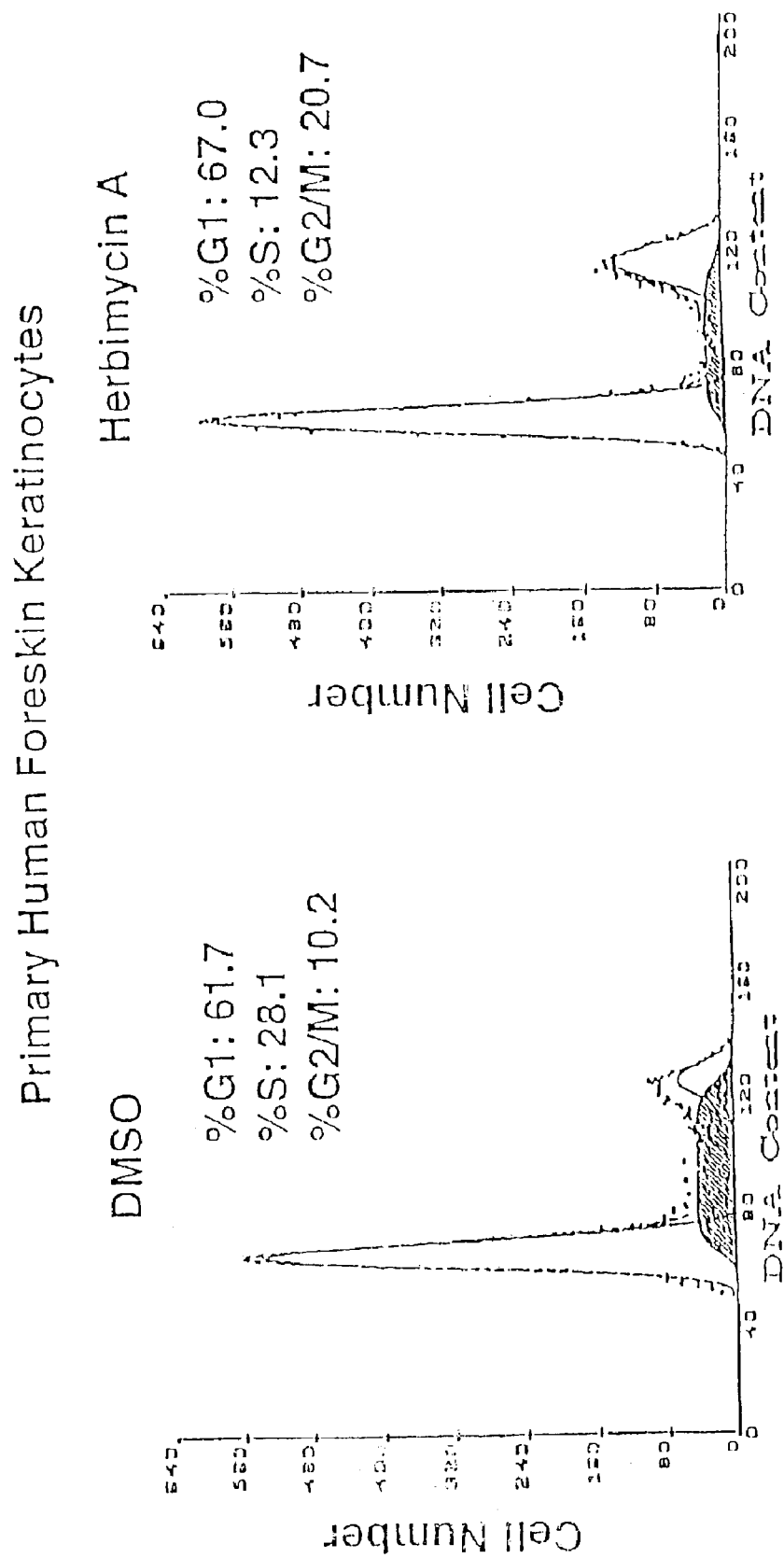
Figure 4B:
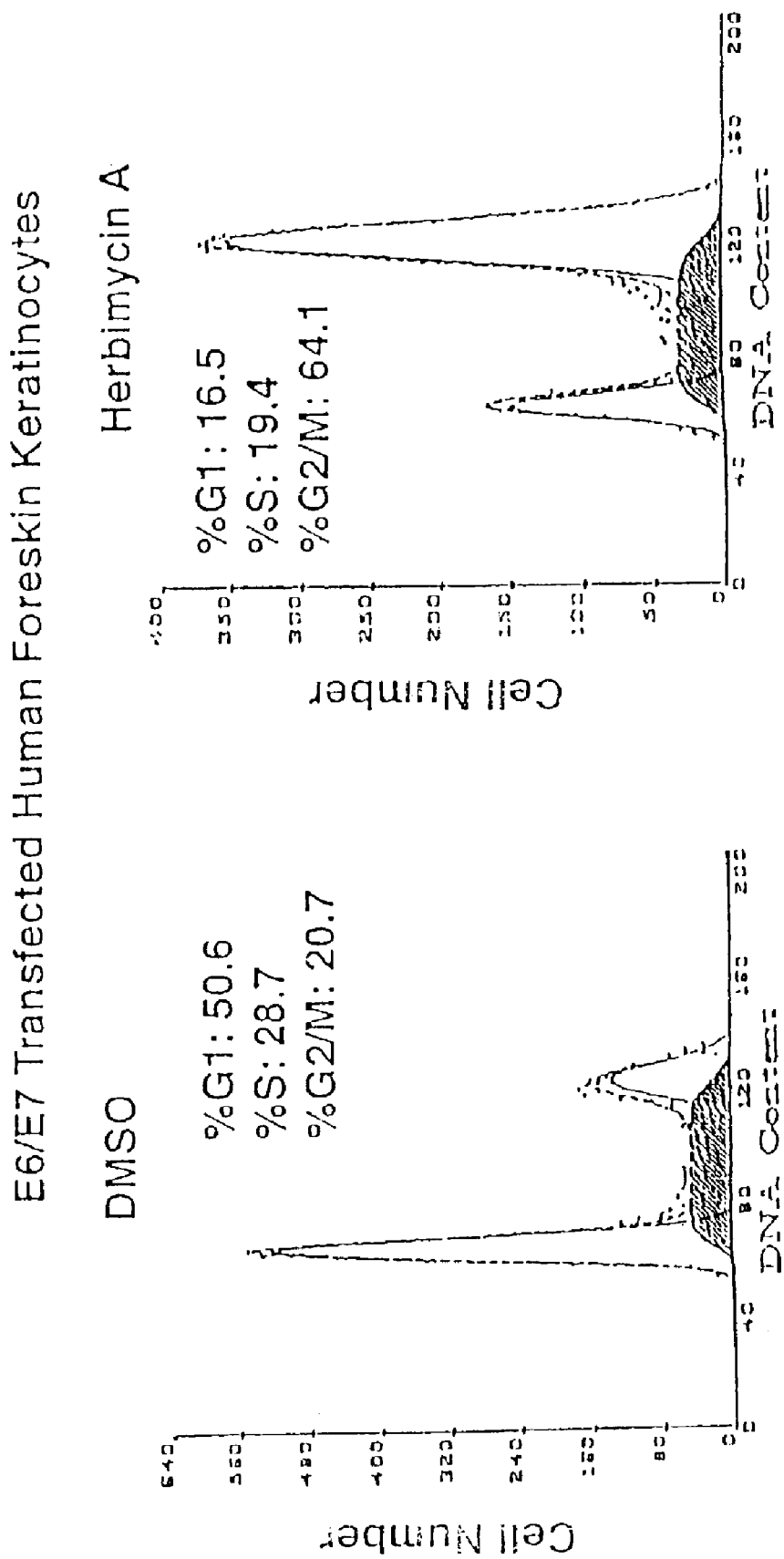

With regard to whether the above observations could result from mutations in other genes that complement with Rb mutations to cause transformation, the cell cycle effects of HA were examined in primary human foreskin keratinocytes (HFK) expressing human papilloma virus-16 (HPV-16) E6 and E7. These viral oncogenes functionally inactivate p53 and Rb, respectively. Introduction of both E6 and E7 was necessary as loss of Rb function in a p53 wild-type background has been shown to predispose cells to undergo apoptosis (Jones, D. L., D. A. Thompson, and K. Munger, 1997, *Virology*, 239:97–107; Pan, H., and A. E. Griep, 1994, *Genes Dev.* 8:1285–99; White, A. E., E. M. Livanos, and T. D. Tlsty, 1994, *Genes Dev.* 8:666–77). While HA caused the majority of primary HFK cells (FIG. 4A) to accumulate in $G_1$, E6/E7 transfectants arrested with 4n DNA content (FIG. 4B). These results provide further evidence that the cell cycle response to the HA is dictated by the status of Rb and moreover, that Rb is required for mitotic traversal following drug exposure. The loss of p53 function alone is not sufficient for mitotic block as the multiple p53-negative/Rb-positive cell lines that have been tested successfully traverse mitosis in the presence of ansamycins.

Figure 5A:
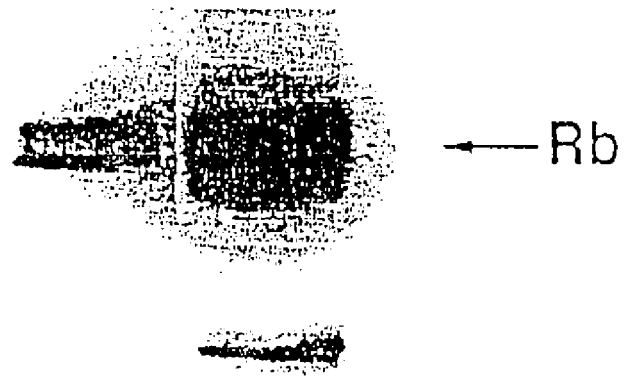
FIG. 5A shows a western blot analysis of Rb expression in MB-MDA 468, 468-7 and 468-19
Figure 5B:
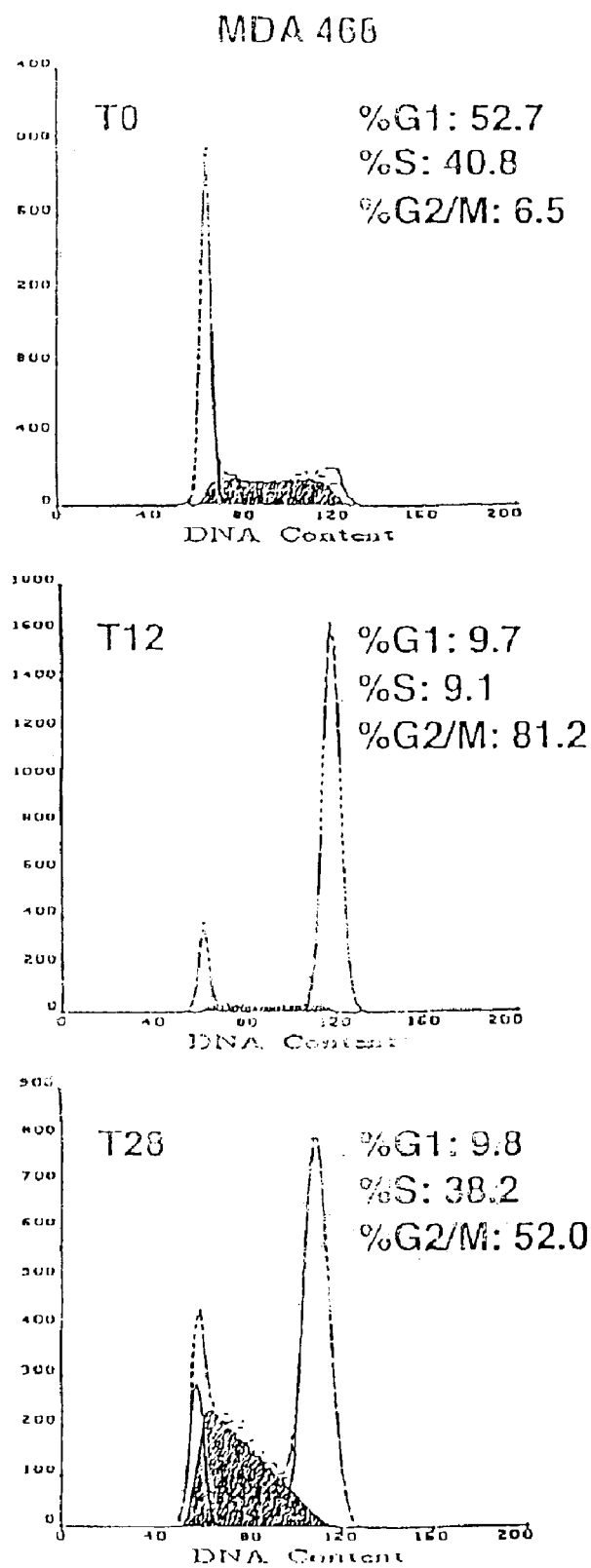
FIGS. 5B–D show that introduction of the Rb gene abrogates HA-induced mitotic arrest in MB-MDA 468 cells.
Figure 5C:
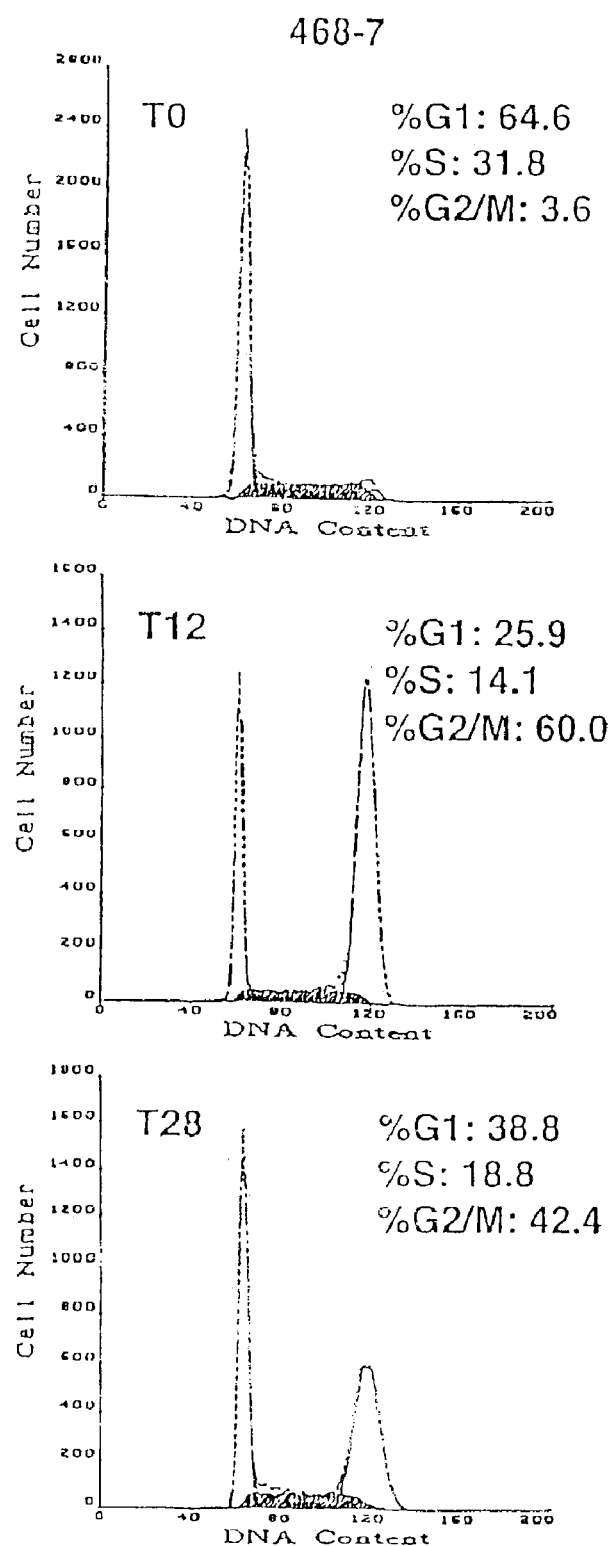
Figure 5D:
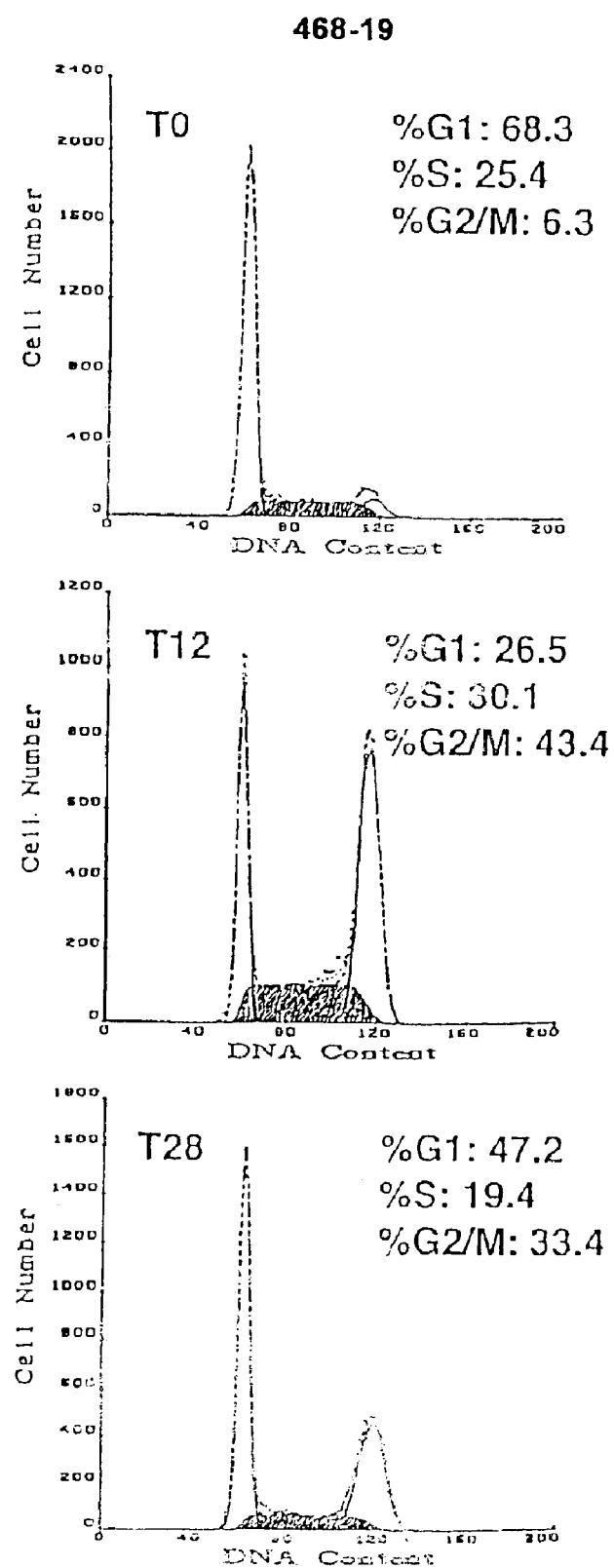

Introduction of Rb into Rb-negative Cells Allows Progression Through M in the Presence of HA The discovery that addition of HA to cells in S phase induces mitotic arrest in Rb negative MB-MDA 468, cells but not Rb-wild type Colo 205 cells indicates that Rb permits progression through mitosis under these conditions. To test this, wild type Rb was reintroduced into the cell line MB-MDA 468. A low transfection efficiency was seen, possibly because elevated expression of Rb inhibits cell growth. Five positive clones were ultimately obtained. These transfectants expressed lower levels of Rb when compared to Rb-wild-type tumor cell lines. Two stably transfected clones expressing different levels of Rb (468-7 and 468-19) were chosen for analysis (FIG. 5A). FACS analysis of logarithmically growing populations revealed that Rb expression in these clones did not alter the cell cycle distribution, though the cells had slightly longer doubling times. When treated with HA, control transfectants accumulated with 4n DNA content. In contrast, the drug had no effect on $G_2$/M in the Rb-transfectants and instead caused an increase in $G_1$. Furthermore, when released from aphidicolin block into HA, both clone 468-7 and 468-19 cycled through mitosis and entered $G_1$, (FIGS. 5C & D). In contrast, when treated with HA after aphidicolin block, MB-MDA 468 cells failed to reach $G_1$ and arrested in mitosis by 12 hours (FIG. 5D). The amount of cell death induced by ansamycins was comparable in the Rb-transfected and untransfected cells. Thus, in the Rb-transfectants, the appearance of a higher percentage of cells in $G_1$ does not result from increased apoptosis of cells in $G_2$/M. As these cell lines differ only in Rb status, this finding demonstrates that Rb expression alone is sufficient to allow progression through mitosis in the presence of HA.

Inhibition of Hsp90 with Radicicol Induces Mitotic Arrest in MB-MDA 468 Cells

HA binds to Hsp90 but may have other effects that relate to its chemical properties. Treatment with GM and 17-AAG generated the same Rb-dependent cell cycle profiles and mitotic phenotype as observed with HA. Radicicol is a non-ansamycin natural product that has been shown to bind to the N-terminal Hsp90 pocket (Schulte, T. et al., 1999, *Mol. Enidocrinol.* 13:1435–1448; Schulte, T. et al., 1998, *Cell Stress Chaperones* 3:100–8) and to induce the degradation of the same spectrum of proteins affected by ansamycins (Soga, S., et al., 1998, *J. Biol. Chest.* 273:822–828). Radicicol treatment induced $G_1$ arrest in Rb-positive cell lines, Colo2O5 and MCF7, but failed to arrest Rb-negative MDA-468 cells in $G_2$, and instead, like ansamycins, caused an accumulation of cells with 4n DNA content. Radicicol-arrested MDA 468 cells also displayed chromosomes localized to the poles as well as strewn along the spindle.

B. Administration and Pharmaceutical Compositions

The compounds utilized in the methods of the instant invention may be administered either alone or in combination with pharmaceutically acceptable carriers, excipients or diluents, in a pharmaceutical composition, according to standard pharmaceutical practice. The compounds can be administered orally or parenterally, including the intraventous, intramuscular, intraperitoneal, subcutaneous, rectal and topical routes of administration.

The pharmaceutical compositions used in the methods of the instant invention can contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions used in the methods of the instant invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The HSP90 inhibitors used in the methods of the present invention may also be administered in the form of a suppositories for rectal administration of the drug. These compositions can be prepared by mixing the inhibitors with a suitable nonirritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing an HSP90 inhibitor can be used. (As used herein, topical application can include mouth washes and gargles.)

The compounds used in the methods of the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The HSP90 inhibitors used in the instant invention may also be co-administered with other well known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of certain viral infections or other conditions associated with an Rb negative phenotype. The instant compounds may also be useful in combination with other inhibitors of parts of the signaling pathway that links cell surface growth factor receptors to nuclear signals initiating cellular proliferation.

The methods of the present invention may also be useful with other agents that inhibit angiogenesis and thereby inhibit the growth and invasiveness of tumor cells, including, but not limited to VEGF receptor inhibitors, including ribozymes and antisense targeted to VEGF receptors, angiostatin and endostatin.

Examples of an antineoplastic agents, which can be used in combination with the methods of the present invention include, in general, alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Example classes of antineoplastic agents includes for example, the anthracycline family of drugs, the vinca drugs, the mitomycins, the bleomycins, the cytotoxic nucleosides, the epothilones, discodermolide, the pteridine family of drugs, diynenes and the podophyllotoxins. Particularly useful members of those classes include, for example, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

When a HSP90 inhibitor used in the methods of the present invention is administered into a human subject, the daily dosage will normally be determined by the prescribing physician with the dosage generally varying according to the age, weight, and response of the individual patient, as well as the severity of the patient's symptoms.

In one exemplary application, a suitable amount of a HSP90 inhibitor is administered to a mammal undergoing treatment for cancer. Administration occurs in an amount of each type of inhibitor of between about 0.1 mg/kg of body weight to about 60 mg/kg of body weight per day, preferably of between 0.5 mg/kg of body weight to about 40 mg/kg of body weight per day. A particular therapeutic dosage that comprises the instant composition includes from about 0.01 mg to about 1000 mg of a HSP90 inhibitor. Preferably, the dosage comprises from about 1 mg to about 1000 mg of a HSP90 inhibitor.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, preferably from about 1 mg to 300 mg, more preferably 10 mg to 200 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The amount and frequency of administration of the HSP90 inhibitors used in the methods of the present invention and if applicable other chemotherapeutic agents and/or radiation therapy will be regulated according to the judgment of the attending clinician (physician) considering such factors as age, condition and size of the patient as well as severity of the disease being treated.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

Also, in general, the HSP90 inhibitor and the chemotherapeutic agent do not have to be administered in the same pharmaceutical composition, and may, because of different physical and chemical characteristics, have to be administered by different routes. For example, the HSP90 inhibitor may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of HSP90 inhibitor, and chemotherapeutic agent and/or radiation will depend upon the diagnosis of the attending physicians and their judgment of the condition of the patient and the appropriate treatment protocol.

The HSP90 inhibitor, and chemotherapeutic agent and/or radiation may be administered concurrently e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with the HSP90 inhibitor.

If the HSP90 inhibitor, and the chemotherapeutic agent and/or radiation are not administered simultaneously or essentially simultaneously, then the initial order of administration of the HSP90 inhibitor, and the chemotherapeutic agent and/or radiation, may not be important. Thus, the HSP90 inhibitor may be administered first followed by the administration of the chemotherapeutic agent and/or radiation; or the chemotherapeutic agent and/or radiation may be administered first followed by the administration of the HSP90 inhibitor. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of the HSP90 inhibitor followed, where determined advantageous, by the administration of the chemotherapeutic agent and/or radiation, and so on until the treatment protocol is complete.

Thus, in accordance with experience and knowledge, the practicing physician can modify each protocol for the administration of a component (therapeutic agent-i.e., HSP90 inhibitor, chemotherapeutic agent or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The following examples are not limiting and are merely representative of various aspects and features of the present invention. All references referred to above and below are incorporated herein by reference.

EXAMPLES

Example 1

Effect of Ansamycins on Cells with a Functional Rb Protein and Cells Lacking a Functional Rb Protein Cell Culture:

The human breast cancer cell lines MB-MDA 468, MCF7 and BT-549 and the colon carcinoma cell line, Colo 205, were obtained from ATCC. Breast cell lines were maintained in DME-F12 media and Colo 205 cells in RPMI; both media were supplemented with 5% fetal calf serum (BRL), 2 mM glutamine and 50 u/ml each of penicillin and streptomycin. All cells were incubated at 37° C. in 5% $CO_2$.

Cells were treated for 24 hours with 250 ng/ml herbimycin A (Gibco) dissolved in DMSO or 435 nM of radicicol (Sigma).

After treatment the nuclei can Do stained wish ethidium bromide and analyzed by flow cytometry.

Flow Cytometry:

Nuclei were isolated for flow cytometry assays stained with ethidium bromide and analyzed using a Becton Dickinson fluorescence-activated cell sorter. Statistical data was obtained using Multicycle program software.

Results:

As shown in FIG. 1, in 12 tumor cell lines examined, ansamycin treatment caused growth arrest in $G_1$. In tumor cell lines with mutated Rb HA treatment failed to induce a $G_1$ block but instead resulted to an accumulation of cells with 4n DNA content (FIG. 1B).

Example 2

Analysis of Cell Arrest in Rb-Negative and Rb-Positive Cells Treated With HSP90 Inhibitors Mitotic Index:

For mitotic indices, cells were typsinized, washed with PBS and fixed with 3% paraformaidehyde in PBS for 20 min. Cells were then stained with 3 µg/ml bisbenzimide (Hoechst 33258; Sigma) for 15 min and examined under fluorescence microscopy. Mitosis was scored by the presence of condensed chromosomes.

Immunofluorescent Analysis:

For immunofluorescent analysis, harvested cells were washed with PBS, fixed with methanol for 20 min at −20° C., washed again and blocked for 30 min with 2% BSA in PBS. Cells were then stained with anti-α-tubulin (Sigma) and anti-centromere protein antibodies (ACA/CREST) (gift of Dr. J. D. Rattner) in 2% BSA PBS for 1 hour. Following 3 washes with 0.5% BSA in PBS, cells were incubated with anti-human FITC conjugated, antimouse rhodamine conjugated antibodies (Molecular Probes) and 2 µg/ml bisbenzimide in 2% BSA in PBS for 45 min. Cells were then washed 4× with 0.5% BSA in PBS, resuspended in PBS and images captured by confocal microscopy or with a CCD camera. Images were then processed using Slidebook 3.0 and Adobe Photoshop program software.

For synchrony experiments, cells were treated with 1 µg/ml aphidicolin (Sigma) for 18 hours, washed and replated in media containing DMSO or HA.

Results:

As shown in FIG. 3, α-tubulin staining demonstrates that arrested cells contained bipolar spindles, indicating that ansamycins do not interfere with spindle formation. Additionally, in most cells, chromosomes localized both to the poles and within the spindle (FIG. 3A): ACA staining revealed paired centromeres on chromosomes at the poles (FIG. 3B). In 77 chromosomes localized to the poles, 87%, scored as double dots for ACA staining, indicating that accumulation of chromosomes at the poles is not the result of premature or incomplete segregation but rather, failure of paired chromatids to assemble to the spindle equator. These data show that HA-treated cells are arrested in promethaphase and that, in Rb-negative cells, HA induces mitotic arrest by interfering with chromosomal alignment.

Example 3

Measurement of Mitotic Cyclins

Immunoblot Analysis:

Levels of mitotic cyclin expression and associated kinase activities in herbimycin arrested MB-MD468 cells were assessed using immunoblot analysis and in vitro kinase assays as described below. Cells cultured with herbimycin were enriched for mitotically arrested cells by using only the loosely adherent population in which the mitotic index was greater than 90%.

Immunoblot analysis of lysates from cells treated with DMSO, nocodazole or herbimycin were analyzed by Western blot analysis using anti-cyclin A or anti-B1 antibodies. Treated cells were harvested, washed with PBS and lysed in NP40 lysis buffer (50 mM Tris pH7.4, 1% NP40,150 mM NaCl, 40 mM NaF. 1 mM Na$_3$VO$_4$, 1 mM phenylmethylsulfonlylfluoride, and 10 µg/ml. each of leupeptin, aprotinin and soybean trypsin inhibitor) for 30 min on ice. Lysates were centrifuged at 15,000×g for 10 min and protein concentration determined by bicinchoninic acid protein assay (Pierce). Equal amounts of total protein were resolved by SDS-PAGE and transferred onto Immobilon PVDF membranes (Millipore) by electroblotting. Blots were blocked overnight in 5% nonfat milk in TBS-T (0.1% Tween-20 TBS, 10 mM Tris pH 7.4, 150 mM NaCl) at 4° C. and subsequently probed with either anti-cyclin A or cyclin B1 antibodies (Santa Cruz Biotechnology). Following incubation with HRP-conjugated secondary antibodies, proteins were detected by chemiluminescence (Amersham).

Immunoprecipitation and In Vitro Kinase Assays:

For immunoprecipitation, 100 µg of total protein was incubated with anticyclin A or anti-cyclin B1 (Santa Cruz) antibodies for 2 hours at 4° C. and then for 1 hour following the addition of protein A-Sephaliose. The immune complexes were washed 4× with lysis buffer and boiled in SDS-PAGE sample buffer for 5 min. Following SDS-PAGE, proteins were transferred onto Immobilon and analyzed by western blotting.

For in vitro kinase reactions, immune complexes were washed 4× with lysis buffer, 2× with kinase buffer (20 mM Tris pH 7.4, 7.5 mM MgCl$_2$, 1 mM DTT) and incubated in 40 µl of kinase buffer containing 2 µg histone H1, 10 µCi [γ-$^{32}$P] ATP and 300 µM ATP for 10 min at 37° C. The reaction was stopped by the addition of SDS-PAGE sample buffer and boiled for 5 min. Proteins were resolved on SDS-PAGE, transferred onto Immobilon and exposed to autoradiography film or phosphoimager screen. Kinase activity was quantitated by FUJIX phosphoimager and MacBAS program software.

Results:

Cyclin B1-associated kinase activity was elevated 5-fold in HA-treated cells when compared to control and was comparable to that seen in nocodazole-arrested cells (FIG. 4B). Cyclin B1 protein expression was also increased in HA-treated cells (FIG. 4B). In contrast, cyclin A expression and its associated kinase activity were slightly lower in both HA and nocodazole-aresseted cells compared to that in control cells (FIG. 4A).

Example 4

Effect of Herbimycin in Cells Expressing Human Papilomma Virus-16 E6 and E7

Primary human foreskin keratinocytes transfected with HPV-1 6 E6 and E7 were provided by Drs. H. Stöppler and R. Schlegel (Georgetown Univ.) and grown as previously described. Primary human foreskin keratinocytes or HPV 16 E6/E7 transfected human foreskin keratinoytes were treated with HA or DMSO for 24 hours and ethidium bromide stained-nuclei analyzed by flow cytometry as described above.

Results:

HA caused the majority of primary HFK cells (FIG. 6A) to accumulate in $G_1$, in contrast E6/E7 transfectants arrested with 4n DNA content (FIG. 6B).

Example 5

Transfection of Rb Gene into Rb-Negative Cells

Rb Transfection:

To further confirm that the gene product of the Rb gene permits progression through mitosis in the presence of an HSP90 inhibitor, MB-MDA 468 cells were transfected with the plasmid pUHD1 0-3HGR containing full-length 4.7 kb human Rb cDNA. Rb transfectants were grown in DME-F12 media supplemented with 5% fetal calf serum (BRL), 2 mM glutamine and 50 µg/ml each of penicillin and streptomycin and 100 µg/ml hygromycin B (Boehringer Mannheim). To confirm the presence of the Rb gene product Western blot analysis was carried out using anti-Rb antibodies (Pharmingen) as described herein. Vector control, MB-MDA 468, and Rb transfected MB-MDA 468 cells were arrested with aphidicolin as described above. After release from aphidicolin arrest, transfected and non-transfected MM-MDA 468 cells were cultured in the presence of an ansamycin inhibitor as described in Example 1. Cell progression was monitored by flow cytometric analysis of ethidium bromide-stained nuclei as described above.

Results:

When treated with HA, control transfectants (MB-MDA 468 cells) accumulated with 4n DNA content. In contrast, in the Rb transfectants (468-7; 468-19) HA caused an increase in $G_1$ and had no effect on $G_2$/M (data not shown). When released from aphidicolin block into HA, Rb transfectants cycled through mitosis and entered $G_1$ (FIGS. 5C–5D). In contrast, when treated with HA after aphidicolin block, MB-MDA 468 cells failed to reach $G_1$ and arrested in mitosis by 12 hours (FIG. 5B).

All patents and publications mentioned in the specification are indicative of the levels of skill of those skilled in the art to which the invention pertains. All references cited in this disclosure are incorporated by reference to the same extent as if each reference had been incorporated by reference in its entirety individually. None of the references are admitted to be prior art.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two tern's. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Other embodiments are within the following claims.

What is claimed is:

1. A method for destroying cells that are deficient in retinoblastoma gene product, comprising administering to said cells a compound capable of inhibiting HSP90 function whereby said cells are destroyed.

2. The method of claim 1, wherein said compound is an ansamycin.

3. The method of claim 2, wherein said ansamycin is selected from the group consisting of geldanamycin, 17-AAG, or herbimycin A.

4. The method of claim 2, wherein said ansamycin is 17-AAG.

5. The method of claim 1, wherein said compound is radicicol.

6. The method of claim 1, wherein said compound is a synthetic compound that binds into the ATP-binding site of a HSP90.

7. A method of treating disorders associated with cells that are deficient in retinoblastoma gene product, comprising administering a therapeutically effective amount of a compound capable of inhibiting HSP90, thereby reducing the number of cells that are deficient in retinoblastoma gene product.

8. A method of treating disorders associated with cells that are deficient in retinoblastoma gene product, comprising administering a therapeutically effective amount of a compound capable of inhibiting HSP90, thereby reducing the number of cells that are deficient in retinoblastoma gene product, wherein said disorder is small cell lung cancer.

9. The method of claim 7, wherein said disorder is associated with a viral infection.

10. The method of claim 9, wherein said viral infection is caused by a Human papilloma virus.

11. The method of claim 9, wherein said disorder is cervical cancer.

12. The method of claim 7, wherein said compound is given in combination with another therapy for treating the disorder.

13. The method of claim 7, wherein said compound is an ansamycin.

14. The method claim 13, wherein said ansamycin is selected from the group consisting of geldanamycin, 17-AAG, or herbimycin A.

15. The method of claim 13, wherein said ansamycin is 17-AAG.

16. The method of claim 7, wherein said compound is radicicol.

17. The method of claim 7, wherein said compound is a synthetic compound which binds in the ATP-binding site of a HSP90.

18. The method of claim 1, wherein said cells are RB negative.

19. The method of claim 7, wherein said cells are RB negative.

* * * * *